(12) United States Patent
Rangheard et al.

(10) Patent No.: US 8,101,762 B2
(45) Date of Patent: Jan. 24, 2012

(54) NITROGEN-CONTAINING ORGANIC COMPOUNDS USABLE AS CATALYTIC COMPOSITION PRECURSORS

(75) Inventors: Claudine Rangheard, Lyons (FR); Helene Olivier-Bourbigou, Saint Genis-Laval (FR); David Proriol, Brignais (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 0 days.

(21) Appl. No.: 12/829,895

(22) Filed: Jul. 2, 2010

(65) Prior Publication Data

US 2011/0009635 A1 Jan. 13, 2011

Related U.S. Application Data

(63) Continuation-in-part of application No. PCT/FR2008/001720, filed on Dec. 10, 2008.

(51) Int. Cl.
*C07D 471/04* (2006.01)
(52) U.S. Cl. ........................................................ 546/88
(58) Field of Classification Search ........................ None
See application file for complete search history.

(56) References Cited

U.S. PATENT DOCUMENTS 6,730,788 B1   5/2004   Helquist

FOREIGN PATENT DOCUMENTS

EP  0816385 A1  1/1998
WO  03011876 A1  2/2003

OTHER PUBLICATIONS

Gibson et al, Bis(imino)pyridines: Surprisingly Reactive Ligands and a Gateway to New Families of Catalysts, 107 Chem. Rev. 1745-1776 (2007).*
World IP Organization. "International Search Report." PCT/FR2008/001720. Applicant: IFP, Mailed: Jul. 21, 2009.
Jie et al. "Iron(II) complexes ligated by 2-imino-1,10-phenanthrolines: Preparation and catalytic behavior toward ethylene oligomerization." (Journal of Molecular Catalysis), pp. 85-96, Apr. 3, 2007, vol. 269, No. 1-2.
Rangheard et al. "Direct synthesis of a new class of N,N,N ligands based on 1,2-dihydro-1,10-phenanthroline backbone and their coordination to Pd complexes." (Journal of Royal Society of Chemistry) pp. 770-772, Dec. 12, 2008, No. 5.

* cited by examiner

*Primary Examiner* — Janet Andres
*Assistant Examiner* — Timothy R Rozof
(74) *Attorney, Agent, or Firm* — Millen, White, Zelano & Branigan, P.C.

(57) ABSTRACT

The present invention describes novel nitrogen-containing organic compounds obtained by reacting a compound X of substituted pyridine type comprising at least one ketone function with a compound Y belonging to the aminoquinoleine family and derivatives thereof. Said organic compounds can be used as precursors in a catalytic composition.

25 Claims, No Drawings

NITROGEN-CONTAINING ORGANIC COMPOUNDS USABLE AS CATALYTIC COMPOSITION PRECURSORS

This application is a continuation-in-part of International Application PCT/FR2008/001720 filed Dec. 10, 2008 and claims priority of French application Ser. No. 08/00.061 filed Jan. 4, 2008.

This application is also related to a concurrently filed application, Ser. No. 12/811,635 entitled "Method of Preparing A Catalytic Composition For Dimerization Co-Dimerization And Oligomerization Of Olfins" by the same inventors and based on PCT/FR2008/001718 filed Dec. 10, 2008 and FR 08/00062 filed Jan. 4, 2008, incorporated by reference herein.

FIELD OF THE INVENTION

The present invention relates to novel nitrogen-containing organic compounds having applications as ligands for transition metals. Said compounds can be used for catalysis, in particular for olefin dimerization, codimerization, oligomerization or polymerization.

BACKGROUND OF THE INVENTION

There are various prospects for linear α-olefins, notably those containing 4 to 20 carbon atoms, depending on the length of their carbon chain. For example C4 to C8 olefins are mainly used as co-monomers for the production of low-density polyethylenes (LLDPE), C8 to C14 olefins as intermediates in the lubricant industry, and C8-C18 olefins for the production of detergents. These olefins experience a strong economic growth. Most industrial α-olefin production processes are ethylene oligomerization methods catalyzed by transition metal complexes.

Incessant research work has been done during the past years to find novel ligands in the sphere of homogeneous catalysis that can lead to more selective, more active and possibly recyclable systems, notably for ethylene polymerization or oligomerization. Nitrogen-containing ligands of bis-imino-pyridine or imino-pyridine type have aroused particular interest, in particular for their adjustable steric and electronic properties and for their tridental or bidental coordination to transition metals. A recently published article (Chem. Rev. 2007, 107, 1745-1776) presents the latest developments achieved around this family of ligands.

Surprisingly enough, we have discovered novel nitrogen-containing organic compounds that can be used in the sphere of homogeneous catalysis.

SUMMARY OF THE INVENTION

The present invention relates to novel nitrogen-containing organic compounds exhibiting a high potential for homogeneous catalysis applications, obtained by reacting a compound X of substituted pyridine type with a compound Y of aminoquinoleine type.

DETAILED DESCRIPTION

The present invention describes the nitrogen-containing organic compound A usable as a ligand in homogeneous catalysis having the general formula as follows:

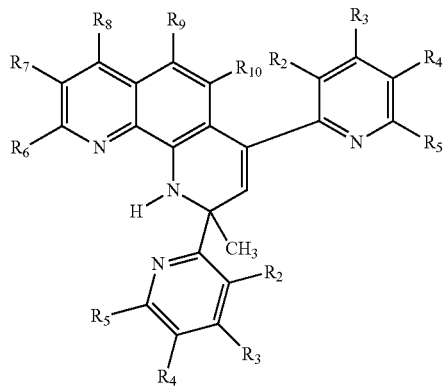

wherein $R_2$ to $R_{10}$, identical or different, are selected from among hydrogen, alkyl groups, saturated or not, cycloalkyl or aromatic, aryl or aralkyl, possibly substituted, alkoxy, aryloxy or amino groups, a halogenide.

In compound A, groups $R_2$ to $R_{10}$, identical or different, can also represent organic radicals wherein one or more hydrogen atoms are replaced by halogenides, a fluoride for example, or groups comprising at least one heteroatom such as oxygen, nitrogen, sulfur, phosphorus or silicon. These heteroelements can be contained in saturated or unsaturated or aromatic alkyl rings.

The present invention describes the nitrogen-containing organic compound B usable as a ligand in homogeneous catalysis having the general formula as follows:

B product

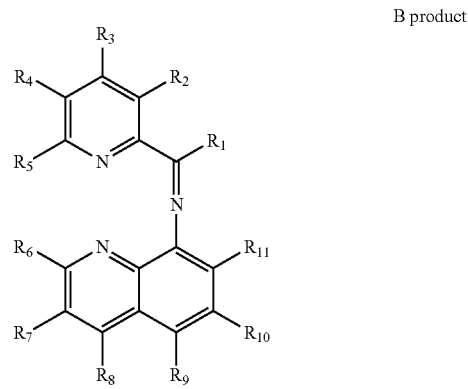

wherein $R_1$ to $R_{11}$, identical or different, are selected from among hydrogen, alkyl groups, saturated or not, cycloalkyl or aromatic, aryl or aralkyl, possibly substituted, alkoxy, aryloxy or amino groups, a halogenide, $R_1$ being different from the methyl radical.

In compound B, groups $R_1$ to $R_{11}$, identical or different, can also represent organic radicals wherein one or more hydrogen atoms are replaced by halogenides, a fluoride for example, or groups comprising at least one heteroatom such as oxygen, nitrogen, sulfur, phosphorus or silicon. These heteroelements can be contained in saturated or unsaturated or aromatic alkyl rings.

The present invention also describes a method of producing products A and B, comprising at least one stage of reacting, preferably in a solvent, a compound X belonging to the substituted pyridine family comprising at least one ketone function with a compound Y belonging to the aminoquinoleine family and their derivatives.

The method according to the invention can also comprise of least one additional stage allowing a group substitution reaction to be carried out.

Compound X meets the general formula as follows:

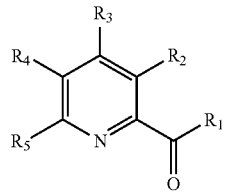

Compound Y belongs to the aminoquinoleine family and their derivatives. The corresponding general formula is as follows:

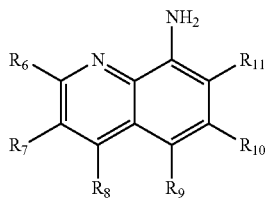

wherein $R_1$ to $R_{11}$, identical or different, are selected from among hydrogen, alkyl groups, saturated or not, cycloalkyl or aromatic, aryl or aralkyl, possibly substituted, alkoxy, aryloxy or amino groups, or halogenides, $R_1$ being different from hydrogen.

Compound X is for example 2-acetylpyridine, 4-methyl-2-acetylpyridine, 2-bromo-6-acetylpyridine, 6-methyl-2-acetylpyridine, 2-methoxy-6-acetylpyridine.

Compound Y is for example 8-aminoquinoleine or 2-methyl-8-aminoquinoleine.

The reaction between the two compounds X and Y is preferably carried out in a solvent, at a temperature preferably ranging between 20° C. and 250° C. Compounds X and Y can be introduced in any order.

The solvents used are selected from among conventional organic solvents, polar or apolar, protic or aprotic, such as aromatic or aliphatic hydrocarbons like toluene, xylene, cyclohexane, chlorinated solvents such as dichloromethane, nitro solvents such as acetonitrile, alcohols such as methanol or ethanol. These solvents can be used alone or in admixture. They are preferably dried, by distillation or by passage through an adsorbent, prior to being used.

The reaction of X with Y is preferably carried out in the presence of a catalyst. The catalysts are preferably selected from among Bronsted acids or Lewis acids.

Bronsted acids are of $H^+X^-$ type wherein $X^-$ represents an anion. $X^-$ anions are preferably selected from among the following anions: tetrafluoroborate, tetraalkylborates, hexafluorophosphates, hexafluoroantimonates, alkylsulfonates (for example methylsulfonate), p-toluenesulfonates, perfluorosulfonates (for example trifluoromethylsulfonate), fluorosulfonates, sulfates, phosphates, perfluoroacetates (for example trifluoroacetate), perfluorosulfonamides (for example bis-trifluoronnethanesulfonyl amidide of formula $N(CF_3SO_2)_2^-$), fluorosulfonamides, perfluorosulfomethides (for example tris-trifluoromethanesulfonyl methylide of formula $C(CF_3SO_2)_3^-$), carboranes, tetraphenylborates and tetraphenylborate anions whose aromatic rings are substituted.

Lewis adds are, by definition, compounds likely to accept an electron doublet.

Examples thereof are lanthanide triflates, in particular ytterbium triflate ($Yb(OTf)_3$), scandium triflate.

The reaction between X and Y can optionally be carried out in the presence of iodine.

The reaction between compounds X and Y releases water. The water can be advantageously trapped during the reaction by adding a desiccant such as a molecular sieve. It can also be removed by azeotropic distillation with the reaction solvent.

The molar ratio between compound X and compound Y ranges between 10 and 0.1, preferably between 5 and 0.2.

The main product obtained upon reaction of X with Y can be isolated and purified according to conventional methods used in organic chemistry, such as precipitation, crystallization or liquid chromatography separation on an alumina or silica column.

The following examples illustrate the invention without limiting the scope thereof.

EXAMPLES

Example 1

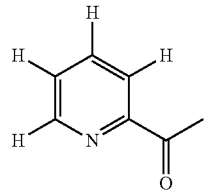

X compound

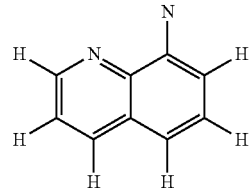

Y compound

Condensation of 6.89 g of 2-acetylpyridine (56.9 mmol) and of 4.1 g of 8-aminoquinoleine (28.4 mmol) with 1.3 mL formic acid HCOOH is carried out in 75 mL anhydrous MeOH. The reaction medium is stirred under reflux for 72 h. After evaporation of the methanol under vacuum, the ketone is evaporated under vacuum and by heating to 60° C. The raw product obtained is purified by chromatography on an alumina column in order to remove the 8-aminoquinoleine, then on neutral silica (eluent $CH_2Cl_2$/AcOEt 80/20). 2.4 g of a yellowish solid are obtained. The yield obtained is 30%.

Characterizations are performed using conventional $^1H$ and $^{13}C$ NMR analysis methods, IR spectroscopy and GC/MS mass spectroscopy.

$^1H$ NMR: $\delta_H$ (300 MHz, $CD_2Cl_2$) 1.90 (s, 3H), 6.17 (d, 1H, J 2.3 Hz), 6.95 (d, 1H, J 8.6 Hz), 7.00 (s, 1H), 7.11 (ddd, 1H, J 7.3, 4.7 and 1.4 Hz), 7.29 (ddd, 1H, J 7.6, 4.7 and 1.2 Hz), 7.32 (d, 1H, J 8.5 Hz), 7.35 (dd, 1H, J 8.2 and 4.35 Hz), 7.49 (dt, 1H, J 7.9 and 1.1 Hz), 7.59 (dt, 1H, J 7.94 and 1.15 Hz), 7.62 (td, 1H, J 7.5 and 1.9 Hz), 7.76 (td, 1H, J 7.65 and 1.2 Hz), 8.02 (dd, 1H, J 8.3 and 1.8 Hz), 8.60 (dq, 1H, J 4.8 and 0.9 Hz), 8.69 (dq, 1H, J 4.9 and 0.9 Hz), 8.75 (dd, 1H, J 4.2 and 1.7 Hz) ppm;

$^{13}$C NMR: δ$_C$ (75 MHz, CD$_2$Cl$_2$) 31.1, 59.1, 113.8, 115.5, 120.3, 121.8, 121.9, 122.7, 123.9, 125.1, 128.9, 130.0, 136.1, 136.5, 136.8, 136.9, 137.7, 140.6, 148.0, 149.61, 149.64, 158.2, 166.6 ppm;

IR: 3371, 3048, 2968, 1632, 1583, 1563, 1508, 1464, 1428, 1378, 1294, 1225, 1100, 1044, 991, 823, 804, 783, 750 cm$^{-1}$.

GC/MS: 350, 335, 272, 256, 167.

The structural formula of the product A obtained is as follows:

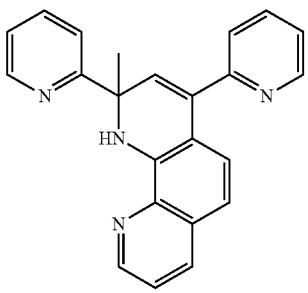

Example 2

The synthesis is achieved as in Example 1, except that 4.00 g of 4-methyl-2-acetylpyridine (29.6 mmol) and 4.27 g of 8-aminoquinoleine (29.6 mmol) are used.

This mixture is brought into solution in 60 mL distilled MeOH with 0.8 mL formic acid, then heated under reflux for 96 hours.

1.8 g of a bright yellow solid is obtained, which corresponds to a 32% yield.

The solid is characterized by $^1$H NMR, $^{13}$C NMR, IR and mass spectroscopy.

$^1$H NMR: δ$_H$ (300 MHz, CD$_2$Cl$_2$) 1.85 (s, 3H), 2.28 (s, 3H), 2.40 (s, 3H), 6.10 (d, 1H, J 2.3 Hz), 6.93 (d, 1H, J 8.6 Hz), 6.96 (m, 1H), 7.12 (dm, 1H, J 5.0 Hz), 7.30-7.40 (m, 4H), 8.01 (dd, 1H, J 8.4 and 1.4 Hz), 8.44 (d, 1H, J 4.9 Hz), 8.52 (d, 1H, J 5.1 Hz), 8.74 (dd, 1H, J 4.2 and 1.7 Hz) ppm;

$^{13}$C NMR: δ$_C$ (75 MHz, CD$_2$Cl$_2$) 21.2, 21.4, 31.2, 59.1, 113.7, 115.4, 121.2, 121.8, 122.9, 123.7, 124.7, 125.3, 128.9, 129.6, 136.1, 136.4, 137.8, 140.6, 147.9, 148.1, 148.2, 149.31, 149.32, 158.2, 166.4 ppm;

IR: 3359, 2974, 2921, 2822, 1640, 1599, 1555, 1509, 1467, 1448, 1423, 1378, 1350, 1116, 1090, 1031, 991, 847, 827, 803, 779, 711, 696 cm$^{-1}$.

MS: EI m/z 363, 286, 270, 256, 243, 189, 181.

The structural formula of the product A obtained is as follows:

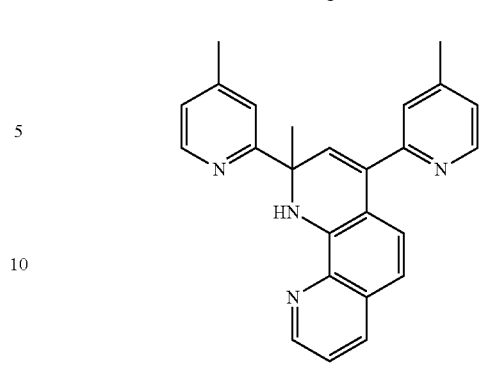

Example 3

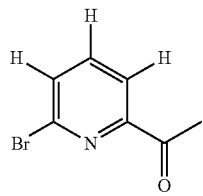

X-compound

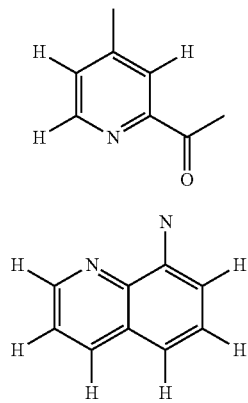

Y-compound

Synthesis of 2-bromo-6-acetylpyridine (Compound X)

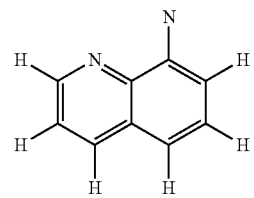

12.5 mL of a solution of n-BuLi 1.6 M in hexane (20 mmol) are added at –78° C. to a solution of 4.70 g 2,6-dibromopyridine 20 (20 mmol) in 100 mL anhydrous ether. The reaction medium is left in the cold for 30 min. 2 mL N,N-dimethylacetamide are added cold (–78° C.) for 1 h, then allowed to reach the ambient temperature. The reaction medium is neutralized with 25 mL of an aqueous HCl 1M solution. The aqueous phase is extracted with Et$_2$O (3×20 mL). The combined organic phases are washed with brine (3×20 mL), dried on MgSO$_4$, filtered, then evaporated under vacuum. The raw product is recrystallized in an Et$_2$O/n-C$_5$H$_{12}$ (1/2) mixture. 1.18 g of an orange solid is obtained, i.e. a 28% yield.

δ$_H$ (300 MHz, CD$_2$Cl$_2$) 2.66 (s, 3H), 7.37 (dd, 1H, J 7.9 and 1.5 Hz), 7.72 (dd, 1H, J 7.9 and 7.0 Hz), 7.96 (dd, 1H, J 7.0 and 1.5 Hz) ppm.

Reaction of 2-bromo-6-acetylpyridine with 8-aminoquinoleine 0.5 g of 2-bromo-6-acetylpyridine (2.5 mmol) and 0.36 g of 8-aminoquinoleine (2.5 mmol) are dissolved in 4.25 mL of freshly distilled methanol. 0.05 mL HCOOH is added and the reaction medium is brought to reflux for 4 days. The precipitate that appears is filtered, then washed with MeOH cold and dried under vacuum. 0.35 g (0.68 mmol) of a pure yellow solid is obtained, which corresponds to a 54% yield.

$^1$H NMR: $\delta_H$ (300 MHz, CD$_2$Cl$_2$) 1.89 (s, 3H), 6.13 (d, 1H, J 2.3 Hz), 6.87 (s, 1H), 7.00 (s, 1H, J 8.7 Hz), 7.27-7.33 (m, 2H), 7.39 (dd, 1H, J 8.4 and 4.2 Hz), 7.43-7.54 (m, 4H), 7.63 (t, 1H, J 7.7 Hz), 8.05 (dd, 1H, J 8.3 and 1.7 Hz), 8.76 (dd, 1H, J 4.2 and 1.7 Hz) ppm;

$^{13}$C NMR: $\delta_C$ (75 MHz, CD$_2$Cl$_2$) 30.5, 59.1, 114.5, 114.8, 119.5, 122.1, 122.9, 124.6, 126.4, 127.2, 129.4, 130.2, 135.5, 136.2, 137.7, 139.4, 139.6, 140.3, 141.8, 142.2, 148.2, 159.0, 168.1 ppm;

IR: 3370, 3064, 1635, 1576, 1548, 1508, 1465, 1441, 1417, 1402, 1375, 1363, 1223, 1184, 1164, 1151, 1119, 1090, 1046, 1019, 986, 922, 848, 823, 797, 770, 746, 705, 696, 668 cm$^{-1}$.

MS: EI m/z 508, 493, 413, 350, 270.

The structural formula of the product A obtained is as follows:

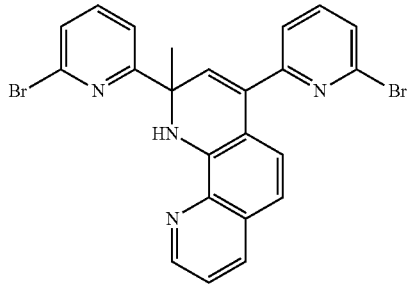

Example 4

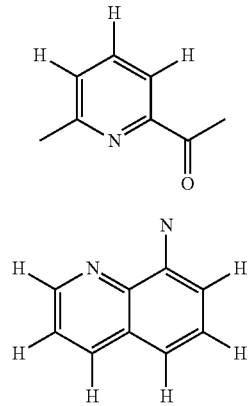

Condensation of 1.95 g of 6-methyl-2-acetylpyridine (14.4 mmol) and of 2.08 g of 8-aminoquinoleine (14.4 mmol) with 0.4 mL formic acid HCOOH is carried out in 30 mL anhydrous MeOH. The reaction medium is stirred under reflux for 96 h. After evaporation of the methanol under vacuum, the raw product is purified on a silica column (eluent: CH2Cl2/ethyl acetate 95/5). 0.8 g of a bright yellow solid is obtained (yield: 17%).

$^1$H NMR: $\delta_H$ (300 MHz, CD$_2$Cl$_2$) 1.87 (s, 3H), 2.54 (s, 3H), 2.59 (s, 3H), 6.12 (d, 1H, J 2.3 Hz), 6.93 (d, H, J 8.7 Hz), 6.94 (s, 1H), 6.97 (dt, 1H, J 7.5 and 0.75 Hz), 7.15 (dm, 1H, J 7.7 Hz), 7.27 (dm, 1H, J 7.3 Hz), 7.29-7.38 (m, 3H), 7.50 (t, 1H, J 7.7 Hz), 7.64 (t, 1H, J 7.7 Hz), 8.01 (dd, 1H, J 8.2 and 1.7 Hz), 8.75 (dd, 1H, J 4.2 and 1.8 Hz) ppm;

$^{13}$C NMR: $\delta_C$ (75 MHz, CD$_2$Cl$_2$) 24.69, 24.72, 31.1, 59.1, 113.7, 115.6, 117.1, 120.9, 121.4, 121.7, 122.1, 125.3, 128.9, 129.9, 136.1, 136.3, 137.1, 137.7, 140.6, 147.9, 157.7, 158.36, 158.49, 165.9 ppm;

IR: 3373, 3055, 2965, 2920, 1733, 1637, 1586, 1572, 1511, 1478, 1456, 1384, 1256, 1225, 1167, 1124, 1099, 1063, 996, 856, 818, 806, 798, 752, 703 cm$^{-1}$.

MS: EI m/z 363, 286, 270, 256, 243, 189, 181.

The structural formula of the product A obtained is as follows:

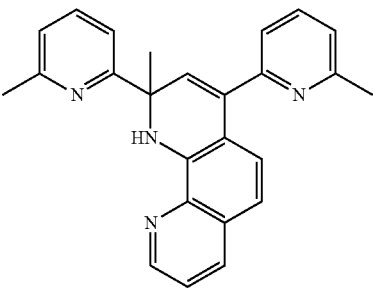

Example 5

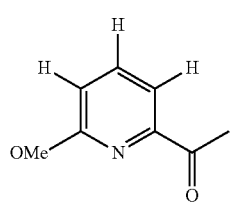

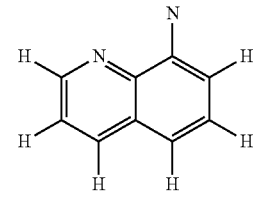

Synthesis of 2-methoxy-6-acetylpyridine

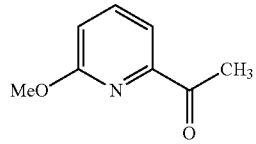

5.1 mL of a solution of n-BuLi 1.6M in hexane (8.14 mmol) are added at −78° C. to a 1 mL (8.16 mmol) solution. The reaction medium is allowed to rise to the ambient temperature for 30 min, 0.81 mL of N,N-dimethylacetamide is added at −78° C. and the reaction medium is stirred cold for 30 min, then allowed to reach the ambient temperature. The reaction medium is neutralized with 1 mL of an aqueous solution of HCl 1 M. The aqueous phase is extracted with Et$_2$O (3×10 mL). The combined organic phases are washed with brine (3×10 mL), dried on MgSO$_4$, filtered, then evaporated under vacuum. 1.03 g (6.08 mmol) of a beige solid is obtained (yield: 84%).

$\delta_H$ (300 MHz, CD$_2$Cl$_2$) 2.65 (s, 3H), 3.99 (s, 3H), 6.93 (dd, 1H, J 7.3 et 0.9 Hz), 7.58 (dd, 1H, J 6.7 and 0.9 Hz), 7.71 (dd, 1H, J 8.8 and 7.3 Hz) ppm.

Reaction of 2-methoxy-6-acetylpyridine with 8-aminoquinoleine 0.5 g of 2-methoxy-6-acetylpyridine (3.3 mmol) and 0.47 g of 8-aminoquinoleine (3.3 mmol) are dissolved in 5.6 mL freshly distilled methanol. 0.07 mL HCOOH is added and the reaction medium is brought to reflux for 4 days, then evaporated under vacuum. The brown oil obtained is purified using a flash chromatography column on silica (eluent: CH$_2$Cl$_2$ 100%, then CH$_2$Cl$_2$/AcOEt, 80/20). A pure solid is obtained.

$^1$H NMR: $\delta_H$ (300 MHz, CD$_2$Cl$_2$) 1.88 (s, 3H), 3.92 (s, 3H), 3.93 (s, 3H), 6.23 (d, 0.1H, J 2.3 Hz), 6.52 (dd, 1H, J 8.3 and 0.6 Hz), 6.74 (dd, 1H, 8.2 and 0.6 Hz), 6.95 (d, 1H, J 8.6 Hz), 7.07 (m, 3H), 7.35 (dd, 1H, J 7.4 and 4.3 Hz), 7.41-7.51 (m, 2H), 7.66 (dd, 1H, J 8.3 and 7.3 Hz), 8.01 (dd, 1H, J 8.3 and 1.6 Hz), 8.73 (dd, 1H, J 4.2 and 1.7 Hz) ppm;

$^{13}$C NMR: $\delta_C$ (75 MHz, CD$_2$Cl$_2$) 31.0, 53.5, 53.6, 58.6, 108.8, 109.8, 112.5, 113.9 (2C), 116.5, 121.2, 125.4, 128.8, 129.9, 136.0, 136.2, 139.3, 139.5 (2C), 141.0, 147.9, 155.9, 163.8, 164.0, 164.6 ppm.

IR: 3384, 2972, 2945, 1630, 1575, 1477, 1461, 1430, 1254, 1053, 797 cm$^{-1}$.

SM: EI m/z: 410, 395, 302, 286, 258.

The structural formula of the product A obtained is as follows:

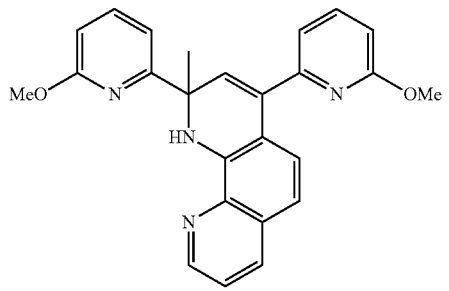

Example 6

1.5 g (2.94 mmol) of product A obtained according to Example 3 and 0.21 g (0.18 mmol) of tetrakispalladium (0) are dissolved in 12 mL toluene. A degassed solution of 1.25 g (11.8 mmol) Na$_2$CO$_3$ in 6 mL distilled water and 0.86 g (7.0 mmol) phenylboronic acid are added. The reaction medium is brought to reflux for 24 h. 4.5 mL of an aqueous solution of 20% NH$_3$ diluted in 30 mL of an Na$_2$CO$_3$ saturated aqueous solution are then added. The aqueous phase is extracted with CH$_2$Cl$_2$ (3×50 mL), the combined organic phases are washed with brine, dried on MgSO$_4$, filtered, then evaporated under vacuum. The raw product is purified using a flash chromatography column (eluent: CH$_2$Cl$_2$ 100%). m=1.56 g. Yield: 44%.

$^1$H NMR: $\delta_H$ (300 MHz, CD$_2$Cl$_2$) 2.01 (s, 3H), 6.37 (d, 1H, J 2.2 Hz), 6.99 (d, 1H, J 8.6 Hz), 7.22 (bs, 1H), 7.36-7.60 (m, 11H), 7.69-7.85 (m, 3H), 8.02-8.12 (m, 5H), 8.8 (dd, 1H, J 4.2 and 1.5 Hz);

$^{13}$C NMR: $\delta_C$ (75 MHz, CD$_2$Cl$_2$) 31.3, 59.3, 114.0, 115.9, 118.4, 118.8, 119.2, 121.8, 122.4, 125.4, 127.3, 128.9, 128.9, 129.0, 129.2, 129.3, 130.3, 136.1, 136.7, 137.8, 137.9, 139.7, 141.2, 148.0, 156.5, 156.7, 158.1, 166.5 ppm.

IR: 3360, 3058, 2964, 1633, 1587, 1564, 1508, 1468, 1441, 1379, 1260, 1158, 1092, 1061, 1026, 989, 814, 800, 760, 692, 659 cm$^{-1}$.

SM: EI m/z: 502, 487, 348, 243.

The structural formula of the product A obtained is as follows:

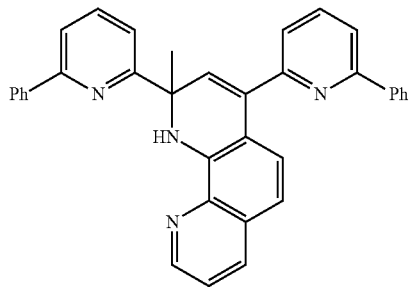

Example 7

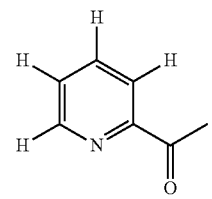

X-compound

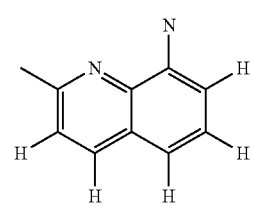

Y-compound

Synthesis of 2-methyl-8-aminoquinoleine (Compound Y) Ziessel, R.; Weibel, N.; Charbonnière, L. S. *Synthesis* 2006, 18, 3128-3133

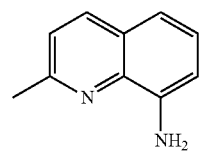

2.110 g of 8-nitroquinaldine (11.19 mmol) are dissolved in 34 mL HI (57% aq). The reaction mixture is heated to 90° C. for 2 h. At ambient temperature, the reaction medium is neutralized with 150 mL of a NaHCO$_3$ saturated aqueous solution. The aqueous phase is extracted with AcOEt (3×50 mL). The combined organic phases are washed with a Na$_2$S$_2$O$_3$ saturated aqueous solution (2×50 mL), then with brine (2×50 ml). The organic phases are dried on MgSO$_4$, filtered and evaporated under vacuum. The raw product is purified using a flash chromatography column on silica (eluent: CH$_2$Cl$_2$ 100%). 1.251 g of a beige solid is obtained. Yield: 89%.

$\delta_H$ (300 MHz, CD$_2$Cl$_2$) 2.69 (s, 3H), 4.96 (bs, 2H, NH$_2$), 6.88 (dd, 1H, J 7.4 and 1.3 Hz), 7.09 (dd, 1H, J 8.1 and 1.3 Hz), 7.25 (m, 2H), 7.96 (d, 1H, J 8.4 Hz); RMN $^{13}$C:

$\delta_C$ (75 MHz, CD$_2$Cl$_2$) 25.0, 109.8, 115.6, 122.2, 126.4, 127.0, 136.0, 137.8, 143.7, 156.3 ppm;

IR: 3467, 3385, 3343, 2365, 3048, 2917, 1616, 1595, 1563, 1507, 1475, 1431, 1373, 1344, 1323, 1284, 1274, 1243, 1137, 1080, 1032, 828, 794, 744, 715, 692 cm$^{-1}$.

SM: EI m/z: 158, 131, 103.

Reaction of 2-acetylpyridine with 2-methyl-8-aminoquinoleine 1 g of 2-methyl-8-aminoquinoleine (6.32 mmol), 1.42 mL of 2-acetylpyridine and a few drops of HCOOH are dissolved in 10 mL of freshly distilled MeOH. The reaction mixture is stirred for 5 days under reflux. The reaction medium is then evaporated under vacuum. The raw product is then purified using a flash chromatography column on silica (eluent: CH$_2$Cl$_2$/AcOEt, 90/10, then AcOEt 100%). 0.823 g of a brown yellow solid is obtained, i.e. a yield of 43%.

$^1$H NMR: $\delta_H$ (300 MHz, CD$_2$Cl$_2$) 1.89 (s, 3H), 2.72 (s, 3H), 6.12 (d, 1H, J 2.3 Hz), 6.89 (d, 1H, J 9.3 Hz), 6.93 (bs, 1H), 7.12 (ddd, 1H, J 7.2, 4.7 and 1.5 Hz), 7.23 (t, 2H, J 7.2 Hz), 7.28 (ddd, 1H, J 7.6, 4.8 and 1.2 Hz), 7.47 (dt, 1H, J 7.8 and 1.1 Hz), 7.56-7.66 (m, 2H), 8.75 (td, 1H, J 7.7 and 1.9 Hz), 7.90 (d, 1H, J 8.4 Hz), 8.60 (ddd, 1H, J 4.7, 1.7 and 0.9 Hz), 8.67 (ddd, 1H, J 4.9, 1.9 and 1.0 Hz) ppm;

$^{13}$C NMR: $\delta_C$ (75 MHz, CD$_2$Cl$_2$) 25.9, 30.8, 59.1, 113.8, 115.5, 120.4, 121.9, 122.6, 122.7, 123.9, 124.1, 136.2, 136.5, 136.8, 136.9, 137.0, 140.0, 149.6 (2C), 156.9, 158.4, 166.8 ppm;

IR: 3373, 3051, 2964, 2921, 1633, 1602, 1584, 1564, 1552, 1516, 1646, 1429, 1385, 1369, 1259, 1090, 1044, 1019, 993, 835, 785, 746, 706, 687 cm$^{-1}$.

SM: EI m/z: 364, 349, 286.

The structural formula of the product A obtained is as follows:

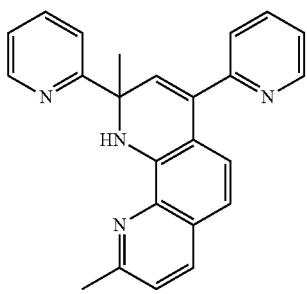

Example 8

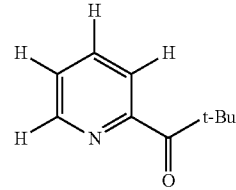
X-compound

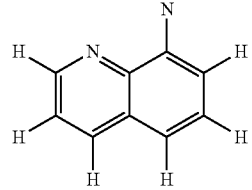
Y-compound 0.85 g (5.2 mmol) of 2,2-dimethyl-1-pyridine-2-ylpropane-1-one, 1.12 g (7.77 mmol) of 8-aminoquinoleine, 15 mL dry toluene and 76 mg (0.4 mmol) of p-toluene sulfonic acid are placed in a drum topped with a modified Dean-Stark separator for recovering the heavier solvent whose tank is filled with 3 Å molecular sieve. The reaction mixture is stirred for 3 days at 150° C. The solvent is then evaporated under vacuum. The 8-aminoquinoleine is eliminated using a chromatography column on alumina (eluent: CH$_2$Cl$_2$/AcOEt, 80/20). The product crystallizes in the initial ketone. The crystals are washed with n-pentane, then vacuum is applied to dry the product. 0.53 g of a nearly translucid solid is obtained (yield: 35%).

$^1$H NMR: $\delta_H$ (300 MHz, CD$_2$Cl$_2$) 1.41 (s, 9H), 6.70 (dd, 1H, J 7.3 and 1.45 Hz), 6.81 (dt, 1H, J 7.8 and 1.15 Hz), 6.93 (ddd, 1H, J 7.9, 5.0 and 1.2 Hz), 7.12-7.24 (m, 2H), 7.28-7.40 (m, 2H), 7.27 (dm, 1H, J 7.3 Hz), 8.02 (dd, 1H, J 8.4 and 1.74 Hz), 8.41 (ddd, 1H, J 5.0, 1.8 and 1.2 Hz) ppm;

$^{13}$C NMR: $\delta_C$ (75 MHz, CD$_2$Cl$_2$) 28.7, 40.7, 118.3, 121.4, 122.4, 122.5, 126.5, 128.9, 135.3, 135.9, 141.4, 148.5, 149.3, 149.6, 157.2, 178.7 ppm;

IR: 3037, 2929, 1644, 15814, 1560, 1496, 1477, 1462, 1426, 1391, 1363, 1311, 1251, 1217, 1079, 1056, 1033, 1002, 986, 830, 809, 791, 756, 721 cm$^{-1}$.

GC/MS: 232, 205, 155, 128, 101, 78, 57

The structural formula of the product B obtained is as follows:

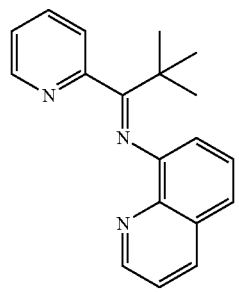

Example 9

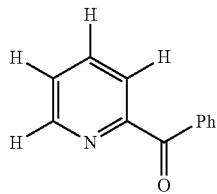

X-compound

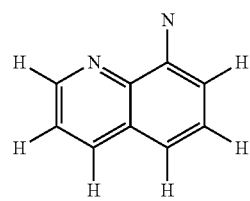

Y-compound 1.48 g (8.08 mmol) of 2-benzoylpyridine, 1.17 g (8.11 mmol) of 8-aminoquinoleine, 25 mL dry toluene and 122.3 mg (0.64 mmol) of p-toluene sulfonic acid are placed in a drum topped with a modified Dean-Stark separator for recovering the heavier solvent whose tank is filled with 3 Å molecular sieve. The reaction mixture is stirred for 3 days at 150° C. The solvent is then evaporated under vacuum. The 8-aminoquinoleine is eliminated using a chromatography column on alumina (eluent: $CH_2Cl_2$/AcOEt, 80/20). The product obtained is solubilized in 30 mL methanol and 120 mL n-heptane are added. The solvents are evaporated through azeotropic distillation intended to eliminate the methanol and to precipitate the desired product. 1.3 g of a yellow solid is obtained (yield: 52%).

IR: 3053, 1641, 1582, 1563, 1494, 1466, 1429, 1379, 1367, 1311, 1244, 1073, 1054, 1027, 993, 958, 829, 792, 764, 754, 740, 723, 713, 638, 616, 599, 583 $cm^{-1}$.

GC/MS: 309, 231, 205, 181, 154, 128, 101, 77, 51

The structural formula of the product B obtained is as follows:

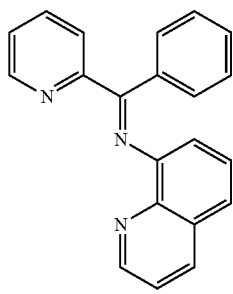

The novel compounds of this invention can be used as ligands in conjunction, with iron, for example, as a transition metal, for the preparation of catalyst composition useful for example for olefin, (ethylene for example) dimerization, co-dimerization, oligomerization or polymerization.

Examples of Catalyst Compositions and Methods

Examples of catalyst compositions and methods of making and using same are found in Applicants' incorporated by reference, concurrently filed application Ser. No. 12/811,635, particularly Examples 1-9 repeated as follows as Examples 1A through 9A:

Example 1A

Synthesis of a Ligand B1

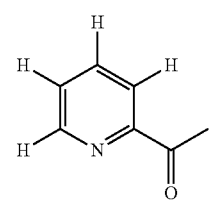

X compound

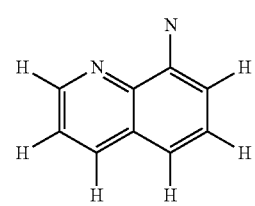

Y compound

Condensation of 6.89 g of 2-acetylpyridine (56.9 mmol) and of 4.1 g of 8-aminoquinoleine (28.4 mmol) with 1.3 mL formic acid HCOOH is carried out in 75 mL anhydrous MeOH. The reaction medium is stirred under reflux for 72 h. After evaporation of the methanol under vacuum, the ketone is evaporated under vacuum and by heating to 60° C. The raw product obtained is purified by chromatography on an alumina column in order to remove the 8-aminoquinoleine, then on neutral silica (eluent $CH_2Cl_2$/AcOEt 80/20). 2.4 g of a yellowish solid are obtained. The yield obtained is 30%.

Characterizations are performed using $^1H$ and $^{13}C$ NMR analysis methods, IR spectroscopy and GC/MS mass spectroscopy.

$^1H$ NMR: $\delta_H$ (300 MHz, $CD_2Cl_2$) 1.90 (s, 3H), 6.17 (d, 1H, J 2.3 Hz), 6.95 (d, 1H, J 8.6 Hz), 7.00 (s, 1H), 7.11 (ddd, 1H, J 7.3, 4.7 and 1.4 Hz), 7.29 (ddd, 1H, J 7.6, 4.7 and 1.2 Hz), 7.32 (d, 1H, J 8.5 Hz), 7.35 (dd, 1H, J 8.2 and 4.35 Hz), 7.49 (dt, 1H, J 7.9 and 1.1 Hz), 7.59 (dt, 1H, J 7.94 and 1.15 Hz), 7.62 (td, 1H, J 7.5 and 1.9 Hz), 7.76 (td, 1H, J 7.65 and 1.2 Hz), 8.02 (dd, 1H, J 8.3 and 1.8 Hz), 8.60 (dq, 1H, J 4.8 and 0.9 Hz), 8.69 (dq, 1H, J 4.9 and 0.9 Hz), 8.75 (dd, 1H, J 4.2 and 1.7 Hz) ppm;

$^{13}C$ NMR: $\delta_C$ (75 MHz, $CD_2Cl_2$) 31.1, 59.1, 113.8, 115.5, 120.3, 121.8, 121.9, 122.7, 123.9, 125.1, 128.9, 130.0, 136.1, 136.5, 136.8, 136.9, 137.7, 140.6, 148.0, 149.61, 149.64, 158.2, 166.6 ppm;

IR: 3371, 3048, 2968; 1632, 1583, 1563, 1508, 1464, 1428, 1378, 1294, 1225, 1100, 1044, 991, 823, 804, 783, 750 $cm^{-1}$.

GC/MS: 350, 335, 272, 256, 167.

The analyses performed allow to propose the following structure for compound B1:

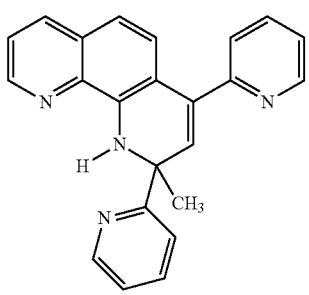

Example 2A

Synthesis of a Ligand B2

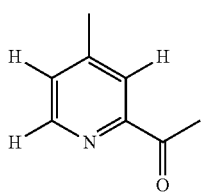 X compound

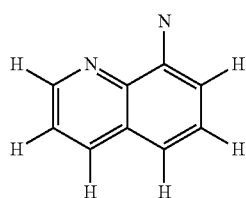 Y compound

Synthesis is achieved as in Example 1A, except that 4.00 g of 4-methyl-2-acetylpyridine (29.6 mmol) and 4.27 g of 8-aminoquinoleine (29.6 mmol) are used.

This mixture is brought into solution in 60 ml distilled MeOH with 0.8 formic acid, then heated under reflux for 96 hours.

1.8 g of a bright yellow solid is obtained, which corresponds to a 32% yield.

The solid is characterized by $^1$H NMR, $^{13}$C NMR, IR and mass spectroscopy.

$^1$H NMR: $\delta_H$ (300 MHz, $CD_2Cl_2$) 1.85 (s, 3H), 2.28 (s, 3H), 2.40 (s, 3H), 6.10 (d, 1H, J 2.3 Hz), 6.93 (d, 1H, J 8.6 Hz), 6.96 (m, 1H), 7.12 (dm, 1H, J 5.0 Hz), 7.30-7.40 (m, 4H), 8.01 (dd, 1H, J 8.4 and 1.4 Hz), 8.44 (d, 1H, J 4.9 Hz), 8.52 (d, 1H, J 5.1 Hz), 8.74 (dd, 1H, J 4.2 and 1.7 Hz) ppm;

$^{13}$C NMR: $\delta_C$ (75 MHz, $CD_2Cl_2$) 21.2, 21.4, 31.2, 59.1, 113.7, 115.4, 121.2, 121.8, 122.9, 123.7, 124.7, 125.3, 128.9, 129.6, 136.1, 136.4, 137.8, 140.6, 147.9, 148.1, 148.2, 149.31, 149.32, 158.2, 166.4 ppm;

IR: 3359, 2974, 2921, 2822, 1640, 1599, 1555, 1509, 1467, 1448, 1423, 1378, 1350, 1116, 1090, 1031, 991, 847, 827, 803, 779, 711, 696 cm$^{-1}$.

MS: EI m/z 363, 286, 270, 256, 243, 189, 181.

The analyses performed allow to propose the following structure for compound B2:

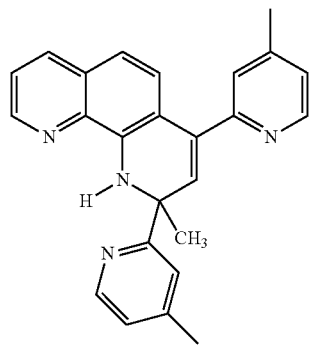

Products Obtained after Contacting Compounds A and B (Stage a))

Example 3A

Synthesis Achieved from Ligand B1 and an Iron Chloride

Ligand B1 described in Example 1A (1.297 g, i.e. 3.7 mmol) and $FeCl_2,4H_2O$ (0.736 g, i.e. 3.7 mmol) are dissolved in 30 mL anhydrous THF. The dark purple reaction medium is stirred for 12 h under argon at ambient temperature. A pink-purple precipitate appears. 7 mL heptane are added, then the medium is filtered by means of a cannula. The pink-purple solid is washed with $Et_2O$ (3×10 mL), then dried under vacuum. 1,742 g of a pink powder is obtained (yield: 99%).

IR: 3144, 2974, 2868, 1602, 1583, 1568, 1500, 1475, 1459, 1432, 1363, 1124, 1059, 1012, 911, 849, 786, 772, 759, 748, 713, 688, 641, 595 cm$^{-1}$.

Elemental analysis for $C_{23}H_{18}Cl_2FeN_4$ C, 58.65; H, 11.12; N, 4.28%.

Exact mass measured: 476.02563.

UV: in $CH_2Cl_2$: 245, 267, 333 and 454 nm.

Mössbauer spectroscopy analysis was carried out and the spectrum of the complex obtained shows a high-spin divalent major iron compound.

Example 4A

Synthesis Achieved from Ligand B2 and an Iron Chloride

The complexation of ligand B2 described in Example 2A is carried out in the same way as in Example 3A.

IR: 3059, 2970, 2866, 1614, 1600, 1557, 1505, 1444, 1368, 1125, 1055, 900, 842, 835, 815, 798, 786, 461 cm$^{-1}$.

Exact mass measured: 504.0558 g.

Example 5A

Synthesis from Ligand B1 and an Iron Bromide

The complexation of ligand B1 described in Example 1A is carried out as in Example 3, but with anhydrous $FeBr_2$. 506 mg of a pink-purple powder are obtained (yield: 89%).

IR: 3144, 3063, 2972, 2868, 1602, 1584, 1557, 1500, 1474, 1460, 1430, 1372, 1117, 1059, 1012, 910, 847, 783, 771, 747, 688, 641 cm$^{-1}$.

Example 6A

Oxidation of the Complex Obtained in Example 3A

The iron complex described in Example 3A (0.200 g) is dissolved in 100 mL previously degassed acetonitrile $CH_3CN$. An $O_2$ stream is passed over the reaction medium for 15 min. The colour of the complex changes from pink to dark purple. The mixture is stirred for one night at ambient temperature under an $O_2$ atmosphere. The reaction medium is then concentrated under vacuum and 20 mL $Et_2O$ are added. The product precipitates. The solid is filtered by means of a cannula then washed with $Et_2O$ (3×10 mL). A black powder is obtained (0.210 g).

IR: 3061, 2967, 1603, 1585, 1566, 1494, 1454, 1396, 1374, 1107, 1051, 1020, 864, 818, 778, 748, 653 cm$^{-1}$.

El. Anal. C, 54.36; H, 3.36; N, 10.61%.

UV: $1.10^{-4}$M in $CH_2Cl_2$: 230, 5; 257, 5; 291; 381; 554; 804 nm.

The Mössbauer spectrum of the sample containing the complex obtained mainly shows the existence of a high-spin Fe(III) compound.

Example 7A

Oxidation of the Complex Obtained in Example 4A

Oxidation of the product obtained in Example 4A is carried out as in Example 6A. The oxidized complex comes in for of a black powder.

IR: 3355, 3049, 2970, 2921, 1663, 1615, 1602, 1558, 1497, 1455, 1392, 1100, 1020, 819, 798, 696 cm$^{-1}$.

Example 8A

Oxidation of the Complex Obtained in Example 5A

Oxidation of the product obtained in Example 5A is carried out as in Example 6A. The oxidized complex comes in form of a black powder.

IR: 3059, 2968, 1668, 1602, 1585, 1566, 1495, 1455, 1393, 1107, 1049, 1019, 992, 820, 776, 749 cm$^{-1}$.

Example 9A

Catalytic Tests

The catalytic test is carried out in a 250-mL, Grignard type reactor provided with a double jacket and a bar magnet. Before the reaction, the reactor is placed under vacuum (approximately $6.10^{-2}$ mbar) and heated to 90° C. for 4 h. After cooling down to ambient temperature, the reactor is pressurized to 3.5 MPa ethylene (0.5 MPa above the planned test pressure) so as to test its tightness throughout one night. The reactor is then heated to 80° C. 42.4 mL distilled toluene, then the MAO solution in toluene (10% in toluene, 200 eq, 2.6 mL), then the catalytic solution ($2.10^{-5}$ moles catalyst in 5 mL toluene) are fed into the reactor under 0.05 MPa ethylene.

The reactor is placed under 3 MPa ethylene pressure. The ethylene pressure is kept constant during the test, the ethylene inflow being controlled by a pressure regulator connected to a ballast placed on a balance. The catalyst activity corresponds to the ethylene consumption measured by the loss of weight of the ballast connected to the reactor and containing the ethylene. The ethylene consumption is measured as a function of time (see curves in the figures). It gives an indication of the catalyst stability over time.

At the end of the reaction, the reactor is depressurized. The gas volume is measured by a gas meter and analyzed. The liquid phase is withdrawn, weighed, and the catalyst is neutralized by adding ethanol. After trap-to-trap vacuum distillation, the liquid phase is analyzed by gas chromatography. A complete balance is performed (material entering, material leaving).

| Complex | Productivity g/g Fe | $C_4$ % weight | % α | $C_6$ % weight | % α | $C_8$ % weight | % α | $C_{10}$ % weight | % α | $C_{12}$ % weight | % α | PE + waxes |
|---|---|---|---|---|---|---|---|---|---|---|---|---|
| complex described in Example 6B | 14050 | 51.4 | 93.9 | 23.8 | 83.6 | 9.8 | 83.8 | 3.1 | 82.4 | 0.6 | — | 11.2 |

Al/Fe: 200 eq,
Fe: $2.10^{-5}$ mol, toluene 50 mL,
P: 30 bar, T: 80° C.,
test duration: 60 min,
MAO: Aldrich, 10% in toluene

| Complex | Productivity g/g Fe | $C_4$ % weight | % α | $C_6$ % weight | % α | $C_8$ % weight | % α | $C_{10}$ % weight | % α | $C_{12}$ % weight | % α | PE + waxes |
|---|---|---|---|---|---|---|---|---|---|---|---|---|
| complex described in Example 7b | 12044 | 40.7 | 97 | 21.7 | 83.8 | 9.4 | 86.0 | 2.1 | 81.8 | 0.3 | — | 25.8 |

Al/Fe: 200 eq
Fe: $2.10^{-5}$ mol, toluene 50 mL,
P: 30 bar, T: 80° C.,
test duration: 60 min,
MAO: Albemarle, 9.2% in toluene

| Complex | Productivity g/g Fe | C4 % weight | C4 % α | C6 % weight | C6 % α | C8 % weight | C8 % α | C10 % weight | C10 % α | C12 % weight | C12 % α | PE + waxes |
|---|---|---|---|---|---|---|---|---|---|---|---|---|
| complex described in Example 8B | 14194 | 44.1 | 95.5 | 21.3 | 84.3 | 7.9 | 84.7 | 2.3 | 80.3 | 0.6 | — | 23.9 |

The invention claimed is:

1. A nitrogen-containing organic compound usable as a precursor ligand in homogeneous catalysis for olefin dimerization, co-dimerization, oligomerization or polymerization, characterized in that it meets the general formula as follows:

Formula A:

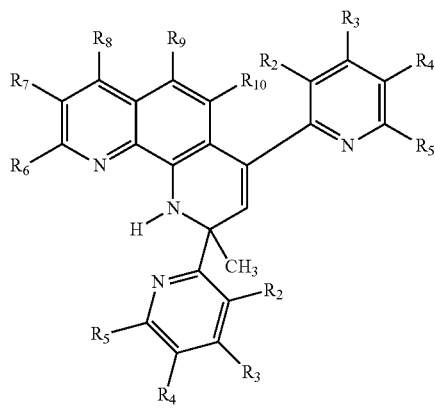

wherein $R_2$ to $R_{10}$, identical or different, are selected from hydrogen, substituted or unsubstituted alkyl groups, saturated or not, substituted or unsubstituted cycloalkyl, substituted or unsubstituted aryl or substituted or unsubstituted aralkyl, substituted or unsubstituted alkoxy, substituted or unsubstituted aryloxy, substituted or unsubstituted amino, or substituted or unsubstituted halogenides.

2. A method of producing product A as claimed in claim 1, comprising at least one stage of reacting, a compound X belonging to the substituted pyridine family comprising at least one ketone function with a compound Y belonging to the aminoquinoleine family and their derivatives, said compound X meeting the general formula as follows:

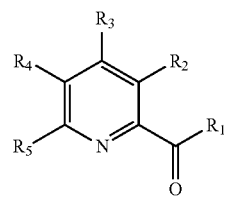

and said compound Y meeting the general formula is as follows:

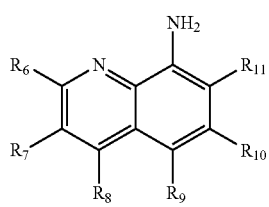

wherein $R_1$ to $R_{11}$, identical or different, are selected from among hydrogen, alkyl groups, saturated or not, cycloalkyl or aromatic, aryl or aralkyl, possibly substituted, alkoxy, aryloxy or amino groups, or halogenides, $R_1$ being different from hydrogen.

3. A method as claimed in claim 2, wherein the temperature ranges between 20° C. and 250° C.

4. A method as claimed in claim 2, wherein the reaction between compound X and compound Y is carried out in a solvent selected from among organic solvents, polar or apolar, protic or aprotic, comprising aromatic or aliphatic hydrocarbons comprising toluene, xylene, cyclohexane, chlorinated solvents comprising dichloromethane, nitro solvents comprising acetonitrile, alcohols comprising methanol or ethanol, alone or in admixture.

5. A method as claimed in claim 2, wherein the reaction between compound X and compound Y is carried out in the presence of a catalyst selected from among Bronsted acids or Lewis acids.

6. A method as claimed in claim 2, wherein water released upon reaction between compounds X and Y is trapped during the reaction by adding a desiccant such as molecular sieve or eliminated through azeotropic distillation with a reaction solvent.

7. A method as claimed in claim 2, wherein the molar ratio between compound X and compound Y ranges between 10 and 0.1.

8. A method as claimed in claim 2, wherein the main product obtained during the reaction of X with Y is isolated and purified by precipitation, crystallization or liquid chromatography separation on an alumina or silica column.

9. A method according to claim 7, wherein said molar ratio ranges between 5 and 0.2.

10. A nitrogen containing organic compound according to claim 1 of the following formula, wherein $R_2$ to $R_{10}$ represents hydrogen:

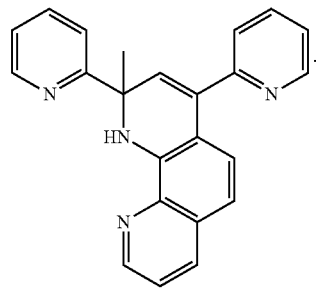

11. A compound according to claim 1, of the following structural formula:

12. A compound according to claim 1, of the following structural formula:

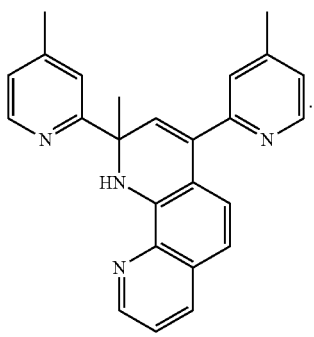

13. A compound according to claim 1, of the following structural formula:

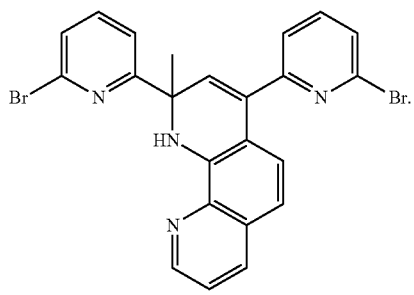

14. A compound according to claim 1, of the following structural formula:

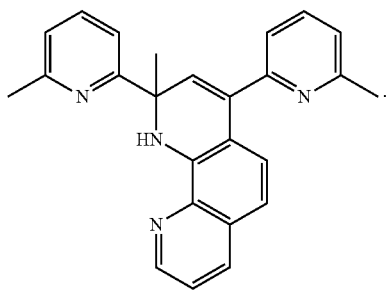

15. A compound according to claim 1, of the following structural formula:

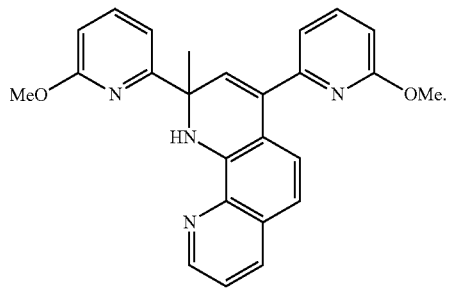

16. A nitrogen-containing organic compound according to claim 1, wherein at least one of $R_2$ to $R_{10}$ is an alkyl group, saturated or not.

17. A nitrogen-containing organic compound according to claim 1, wherein at least one of $R_2$ to $R_{10}$ is a cycloalkyl group substituted or unsubstituted.

18. A nitrogen-containing organic compound according to claim 1, wherein at least one of $R_2$ to $R_{10}$ is an aryl group substituted or unsubstituted.

19. A nitrogen-containing organic compound according to claim 1, wherein at least one of $R_2$ to $R_{10}$ is an alkoxy group substituted or unsubstituted.

20. A nitrogen-containing organic compound according to claim 1, wherein at least one of $R_2$ to $R_{10}$ is an aralkyl group substituted or unsubstituted.

21. A nitrogen-containing organic compound according to claim 1, wherein at least one of $R_2$ to $R_{10}$ is an aryloxy group substituted or unsubstituted.

22. A nitrogen-containing organic compound according to claim 1, wherein at least one of $R_2$ to $R_{10}$ is an amino group substituted or unsubstituted.

23. A nitrogen-containing organic compound according to claim 1, wherein at least one of $R_2$ to $R_{10}$ is a halogenide group substituted or unsubstituted.

24. A compound according to claim 1 of a group consisting of compounds of any of the following formulae:

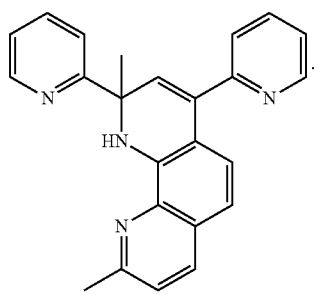

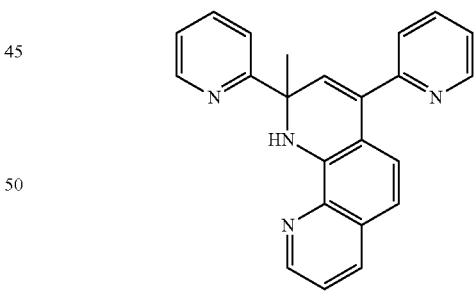

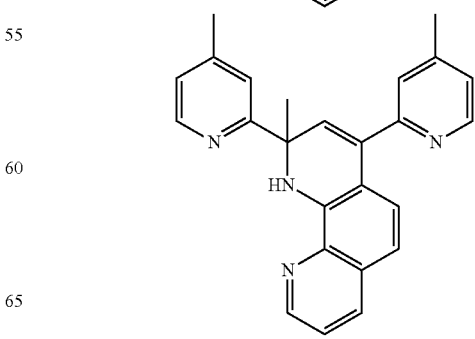

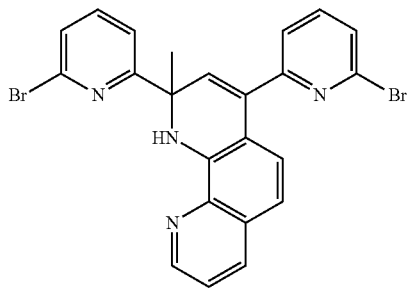
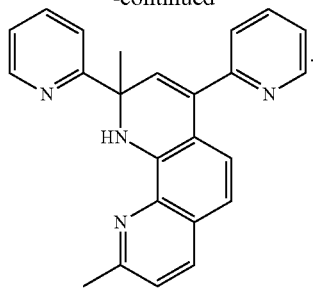

25. A nitrogen-containing organic compound usable as a precursor ligand in homogeneous catalysis for olefin dimerization, co-dimerization, oligomerization or polymerization, characterized in that it meets the general formula as follows:

Formula A:

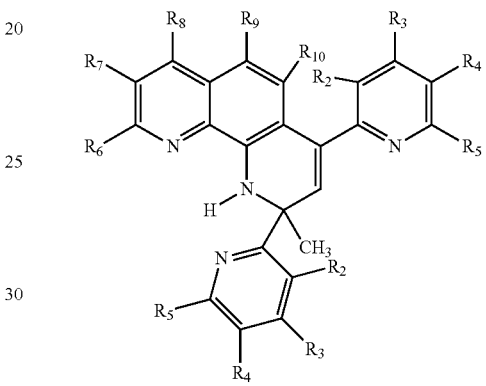

wherein $R_2$ to $R_{10}$, identical or different, represent organic radicals wherein one or more hydrogen atoms are replaced by halogenides, fluoride, or saturated or unsaturated aromatic or cycloalkyl rings comprising at least one heteroatom selected from oxygen, nitrogen, sulfur, phosphorous or silicon.

* * * * *

UNITED STATES PATENT AND TRADEMARK OFFICE
CERTIFICATE OF CORRECTION

| | | |
|---|---|---|
| PATENT NO. | : 8,101,762 B2 | Page 1 of 1 |
| APPLICATION NO. | : 12/829895 | |
| DATED | : January 24, 2012 | |
| INVENTOR(S) | : Claudine Rangheard et al. | |

It is certified that error appears in the above-identified patent and that said Letters Patent is hereby corrected as shown below:

On The Title Page:

After Item (65), insert the following:

Item --(30) Foreign Application Priority Data

Jan. 4, 2008     (FR)            08 0061--

Signed and Sealed this
Twentieth Day of March, 2012

David J. Kappos
*Director of the United States Patent and Trademark Office*